(12) United States Patent
Bertagnoli

(10) Patent No.: US 9,357,985 B2
(45) Date of Patent: Jun. 7, 2016

(54) METHOD FOR ACCESSING A SPINAL FACET JOINT

(75) Inventor: Rudolf Bertagnoli, Straubing (DE)

(73) Assignee: Spinal Elements, Inc., Carlsbad, CA (US)

( * ) Notice: Subject to any disclaimer, the term of this patent is extended or adjusted under 35 U.S.C. 154(b) by 1153 days.

(21) Appl. No.: 12/121,293

(22) Filed: May 15, 2008

(65) Prior Publication Data
US 2009/0287262 A1   Nov. 19, 2009

(51) Int. Cl.
*A61B 17/02* (2006.01)

(52) U.S. Cl.
CPC .............. *A61B 17/02* (2013.01); *A61B 17/0206* (2013.01); *A61B 17/0293* (2013.01)

(58) Field of Classification Search
CPC .............. A61F 2/4405; A61B 17/1671; A61B 17/7064; A61B 17/1757
USPC ........................................................ 606/86 A
See application file for complete search history.

(56) References Cited

U.S. PATENT DOCUMENTS

| | | | |
|---|---|---|---|
| 5,741,261 A * | 4/1998 | Moskovitz et al. | 606/79 |
| 6,733,533 B1 * | 5/2004 | Lozier | 623/17.12 |
| 7,396,360 B2 * | 7/2008 | Lieberman | 606/247 |
| 2002/0022764 A1 * | 2/2002 | Smith et al. | 600/114 |
| 2003/0204189 A1 * | 10/2003 | Cragg | 606/61 |
| 2004/0176763 A1 * | 9/2004 | Foley et al. | 606/60 |
| 2005/0177240 A1 * | 8/2005 | Blain | 623/17.15 |
| 2005/0197660 A1 * | 9/2005 | Haid et al. | 606/61 |
| 2005/0203529 A1 * | 9/2005 | Boehm et al. | 606/86 |
| 2006/0004367 A1 * | 1/2006 | Alamin et al. | 606/74 |
| 2006/0030850 A1 | 2/2006 | Keegan | |
| 2006/0111779 A1 * | 5/2006 | Petersen | 623/17.11 |
| 2006/0235388 A1 * | 10/2006 | Justis et al. | 606/61 |
| 2006/0264953 A1 * | 11/2006 | Falahee | 606/72 |
| 2008/0255563 A1 * | 10/2008 | Farr et al. | 606/79 |

FOREIGN PATENT DOCUMENTS

WO   WO 2005/032358 A2   4/2005

OTHER PUBLICATIONS

International Search Report for International App. No. PCT/US2009/044029, dated Jul. 13, 2009.
International Preliminary Report on Patentability for International App. No. PCT/US2009/044029, dated Nov. 17, 2010.

* cited by examiner

*Primary Examiner* — Bruce Snow
*Assistant Examiner* — Melissa Hoban

(57) ABSTRACT

A minimally invasive method for accessing a facet joint of the spine is provided. Embodiments of the method include creating a small incision directly over the facet joint and to allow direct access and visualization of the joint. A second incision, which may be a puncture wound, is provided at a distance from the first incision. A path between the second incision and the facet joint is then formed which may be curved or substantially straight. The path is preferably configured to intersect both facet surfaces. The path may be formed using an instrument which can be used to drill a hole across the facets, insert a fastener across the facets, or the like.

33 Claims, 7 Drawing Sheets

METHOD FOR ACCESSING A SPINAL FACET JOINT

FIELD OF THE INVENTION

The present invention relates to a method for accessing a vertebral facet joint.

BACKGROUND OF THE INVENTION

Traumatic, inflammatory, and degenerative disorders of the spine can lead to severe pain and loss of mobility. For example, back and spinal musculoskeletal impairments are significant causes of lost work productivity in the United States. Pain as a result of some type of spinal impairment may have its source in a variety of pathologies or clinical conditions.

As shown in FIG. 1, the vertebral column 2 of the spine includes a series of alternating vertebrae 4 and fibrous discs 6 that provide axial support and movement to the upper portions of the body. The vertebral column 2 typically includes thirty-three vertebrae 4, with seven cervical (C1-C7), twelve thoracic (T1-T12), five lumbar (L1-15), five fused sacral (S1-S5) and four fused coccygeal vertebrae.

FIGS. 2A and 2B depict a typical thoracic vertebra. Each vertebra includes an anterior body 8 with a posterior arch 10. The posterior arch 10 has two pedicles 12 and two laminae 14 that join posteriorly to form a spinous process 16. Projecting from each side of the posterior arch 10 is a transverse 18, superior 20 and inferior articular process 22. The facets 24, 26 of the superior 20 and inferior articular processes 22 form facet joints 28, or zygapophysial joints, where they align with the articular processes of the adjacent vertebrae, as shown in FIGS. 3A and 3B. The facet joints are true synovial joints, with cartilaginous surfaces and a joint capsule.

The orientation of the facet joints vary, depending on the level of the vertebral column. FIGS. 4A to 6B depict the orientations of the facet joints at different levels of the vertebral column. In the C1 and C2 vertebrae (not shown), the facet joints are substantially parallel to the transverse plane.

In the C3 to C7 vertebrae shown in FIGS. 4A and 4B, the facets are oriented at an approximately 45-degree angle to the transverse plane 30 and are substantially parallel to the frontal plane 32. This orientation allows the facet joints of the cervical vertebrae to flex, extend, laterally flex, and rotate. The 45-degree angle orientation with respect to the transverse plane 30 allows the facet joints of the cervical spine to guide the movement of the cervical vertebrae without limiting such movement.

FIGS. 5A and 5B depict the thoracic vertebrae, which include facets oriented at an approximately 60-degree angle to the transverse plane 30 and an approximately 20-degree angle to the frontal plane 32. This orientation is capable of allowing lateral flexion and rotation, but only limited flexion and extension.

FIGS. 6A and 6B illustrate the lumbar region, where the facet joints are oriented at approximately 90-degree angles to the transverse plane 30 and an approximately 45-degree angle to the frontal plane 32. The lumbar vertebrae allow flexion, extension and lateral flexion of the lumbar region, but little, if any, rotation because of the 90-degree orientation of the facet joints in the transverse plane. The actual range of motion along the vertebral column can vary considerably with each individual vertebra.

In addition to guiding movement of the vertebrae, the facet joints also contribute to the load-bearing ability of the vertebral column. For example, facet joints can bear up to 30% of the load on the spine in some positions of the vertebral column as described, e.g., in King et al., Mechanism of Spinal Injury Due to Caudocephalad Acceleration, Orthop. Clin. North Am., 6:19 (1975). The facet joints may also play a role in resisting shear stresses between the vertebrae. Over time, these forces acting on the facet joints can cause degeneration and arthritis.

One source of back and spine pain is related to degeneration of the facets of the spine or facet arthritis. Bony contact or grinding of degenerated facet joint surfaces between two vertebrae may play a role in some pain syndromes. Such degenerative problems with the facet joints are often treated by fusing the two adjacent vertebrae together. By performing this surgical procedure, the relative motion between the two adjacent vertebrae is effectively stopped. This fusion procedure significantly reduces relative motion of the facets between the adjacent vertebrae. However, the facets between fused vertebrae may still exhibit some relative motion as the vertebral column is subjected to overall movement and various stresses. Such motion can lead to further problems, such as pain, arising from the degenerative facet joint.

Often, the facet joints between fused vertebrae are not treated as part of the fusion procedure. In certain procedures, the facets may be screwed together, or otherwise affixed to one another. Such a procedure generally requires access to the facet joints at a particular angle, for example, to affix a screw or other fastener between the facets. However, because the facets can have various orientations with respect to the surface of the back, providing such access is often achieved by creating large incisions or wounds over the facet of interest. Such large incisions can require long healing times, may be susceptible to infection, and also may form unsightly scars after healing.

Certain techniques for addressing facet joint problems include providing an implant in the facet joint to facilitate smooth movement in the joint. Such a technique is described, e.g., in U.S. Patent Publication No. 2005/0177240. The technique described in this publication includes providing an implant within a facet joint which includes a hole therethrough, drilling of a hole through the adjacent facets of the joint, and subsequent insertion of a retaining member through the holes in the facets and implant. Drilling of the holes in the facets (and optionally drilling of a hole in the inserted implant at the same time) also requires access to the facet joint. Preferably, a drill can be oriented at an approximately perpendicular direction to the articular surfaces of the facet joint. Such orientation allows formation of a hole through the facets that can be used effectively to secure an implant within the joint. It is also desirable to provide direct observation of the facet joint during such a drilling procedure to ensure that the hole is properly located. As described above, providing such particular access to a facet joint is generally achieved by creating a large incision through the tissue overlying the facet joint to expose the joint and provide the desired access thereto.

Accordingly, there is a need to access a facet joint that is minimally invasive, allows direct visualization of the joint, and provides direct access along a path approximately perpendicular to the articular surfaces of the facet joint.

SUMMARY OF THE INVENTION

Embodiments of the present invention provide a method for providing access to a facet joint which allows both direct visualization of the joint and which further provides a path for an instrument that intersects the articular surfaces of the joint, preferably at an angle that is close to 90 degrees. The method further provides such access in a minimally invasive manner, which avoids creation of large incisions that require extensive healing and which may leave scars.

In one aspect, embodiments of the invention provide a method for accessing a spinal facet joint which includes providing a first incision over the facet joint, retracting sides of the first incision to reveal the facet joint, and creating a second incision at a particular distance and orientation relative to the first incision which allows formation of a path between the second incision and the facet joint, where the path is substantially orthogonal to a facet surface of the facet joint in the vicinity of the joint. Non-orthogonal angles between the path and the facet surfaces may also be used. Preferably, such angles are close to 90 degrees, such that the path intersects a portion of the surfaces of both facets. The distance between the first incision and the second incision is preferably between about 2 cm and about 20 cm, or more preferably between about 2 cm and about 10 cm, although distances outside of these ranges may also be used for particular applications.

In one embodiment, the path is substantially straight between the second incision and the first incision. In a further embodiment, the path is curved. Such a curved path can allow more flexibility in selecting a location for the second incision with respect to the first incision.

The sides of the first incision can be retracted using, e.g., a tissue retractor to facilitate access to and visualization of the facet joint. The tissue retractor can be a blade retractor, a tubular retractor, or another conventional tissue retractor. Tissue between the first incision and the facet joint can be cut away to allow direct physical and visual access to the facet joint. For example, this access can be used to open the joint capsule surrounding the facet joint, and optionally to remove some or all of the cartilage present in the joint. The facet surfaces in the joint can also be prepared for accepting an implant. Such preparation can include roughening the facet surfaces.

The path between the second incision and the facet joint can be created by inserting an instrument through the second incision and pushing it through the muscle and other tissue until it reaches the joint. The instrument can include a cylindrical or tubular housing, which may be substantially straight or curved along the main axis thereof, and a tip of the instrument can be sharp or blunt. The instrument can be used to drill or otherwise create a hole through the facets of the facet joint, and optionally create a further hole through an implant if one is provided within the facet joint. These holes can be configured to accept a retaining member configured to maintain an implant within the facet joint. Alternatively, the instrument can be used to insert a fastener, such as a screw, across the facets to immobilize the facet joint. After the facet joint is treated, the incisions are closed and allowed to heal.

BRIEF DESCRIPTION OF THE DRAWINGS

Further objects, features and advantages of the invention will become apparent from the following detailed description taken in conjunction with the accompanying figures showing illustrative embodiments, results and/or features of the present invention, in which.

Figure 1:
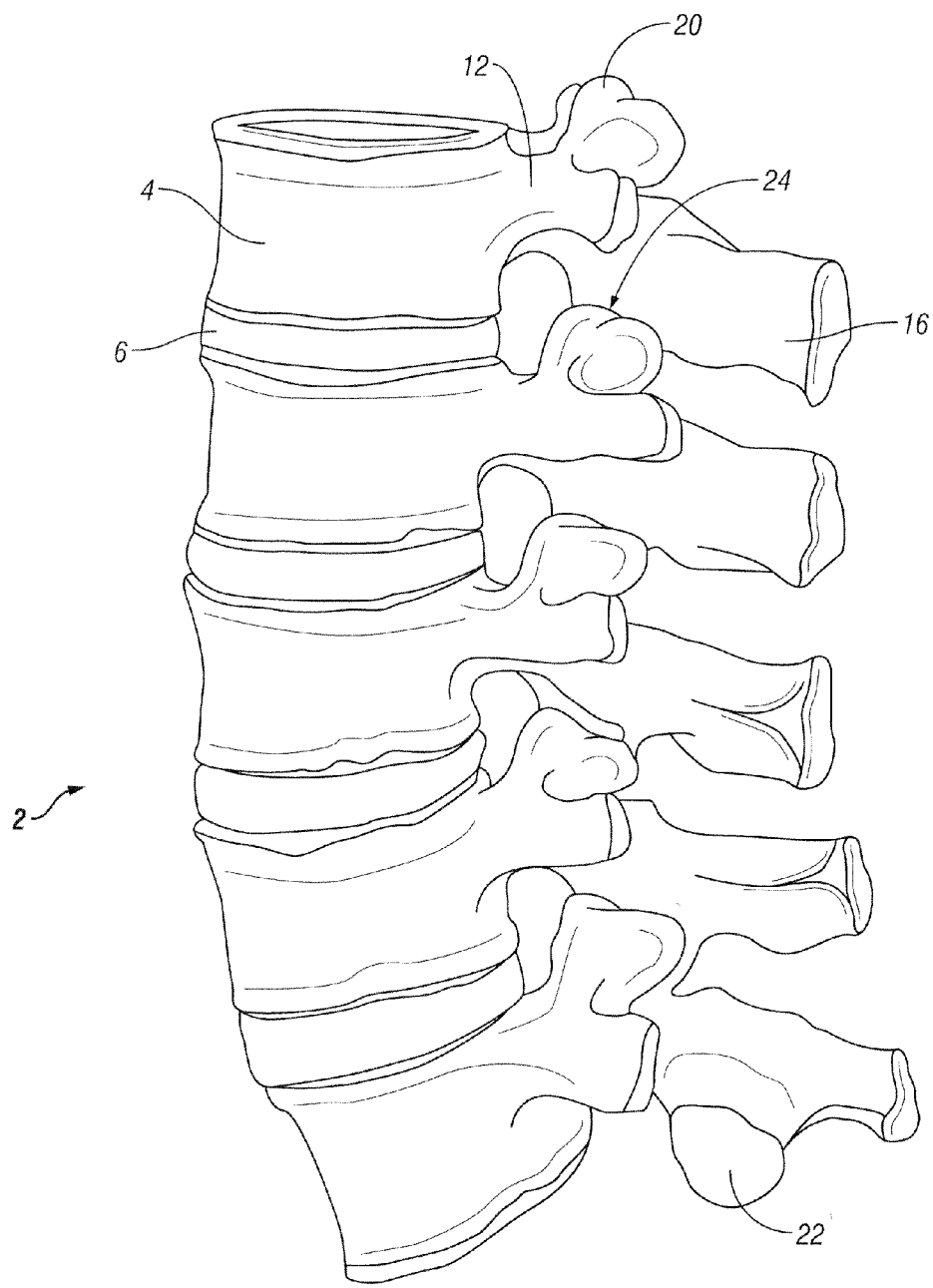
FIG. 1 is a lateral elevational view of a portion of the vertebral column.
Figure 2A:
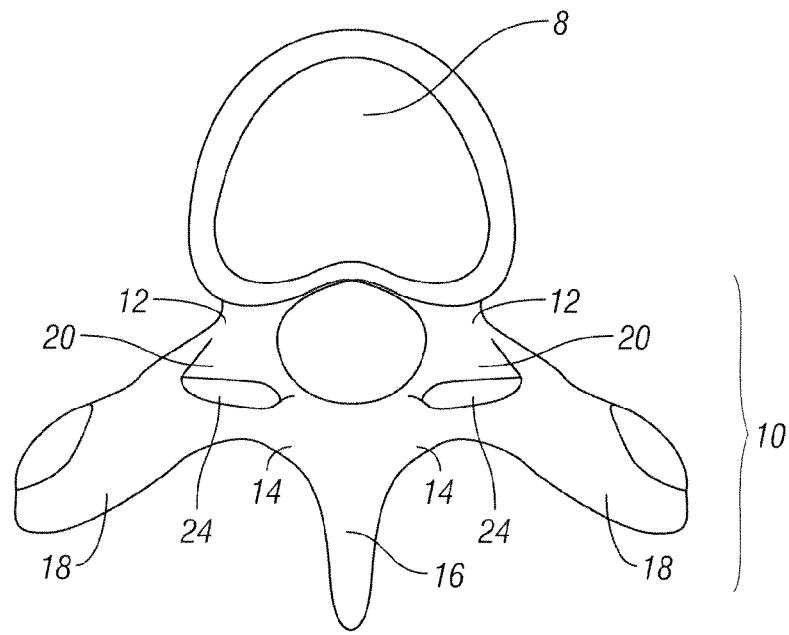
FIGS. 2A and 2B are schematic superior and side views, respectively, of an isolated thoracic vertebra.
Figure 2B:
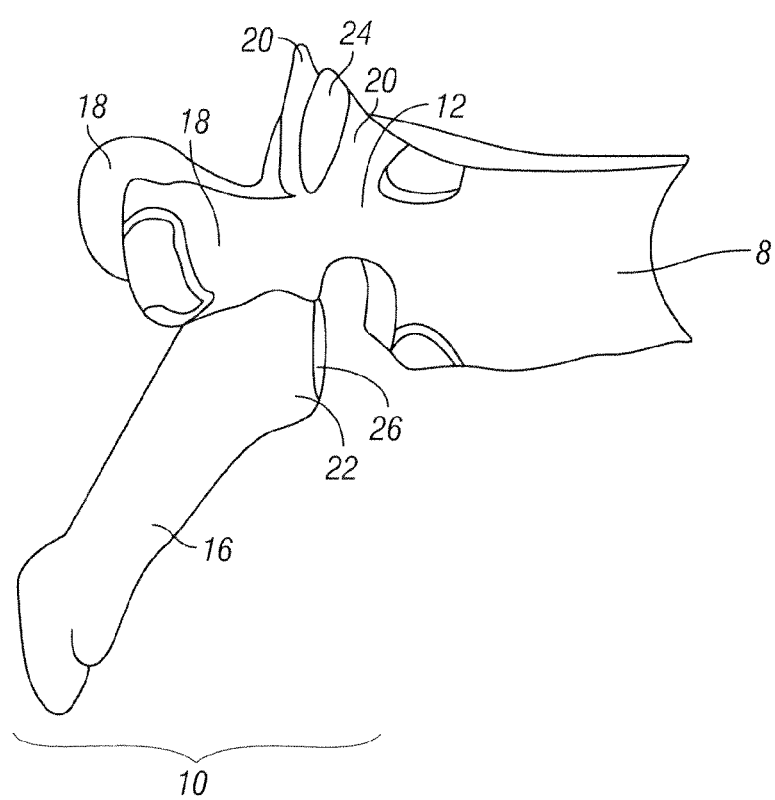
Figure 3A:
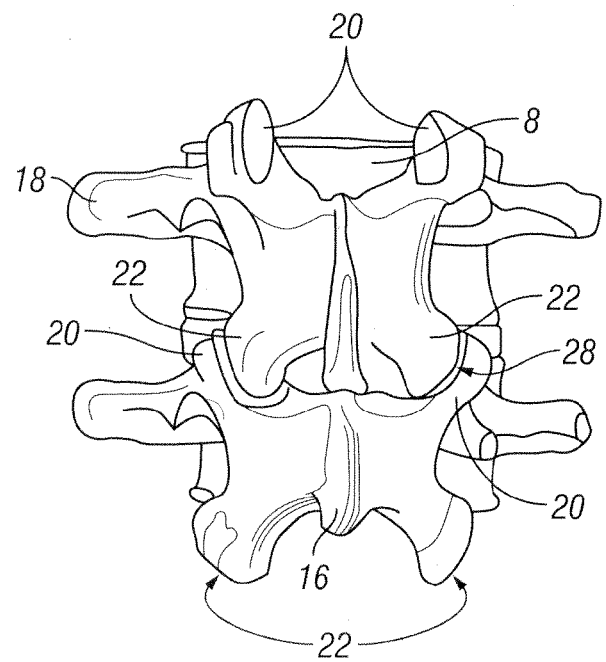
FIGS. 3A and 3B are schematic posterior and posterior-oblique elevational views, respectively, of a portion of the vertebral column.
Figure 3B:
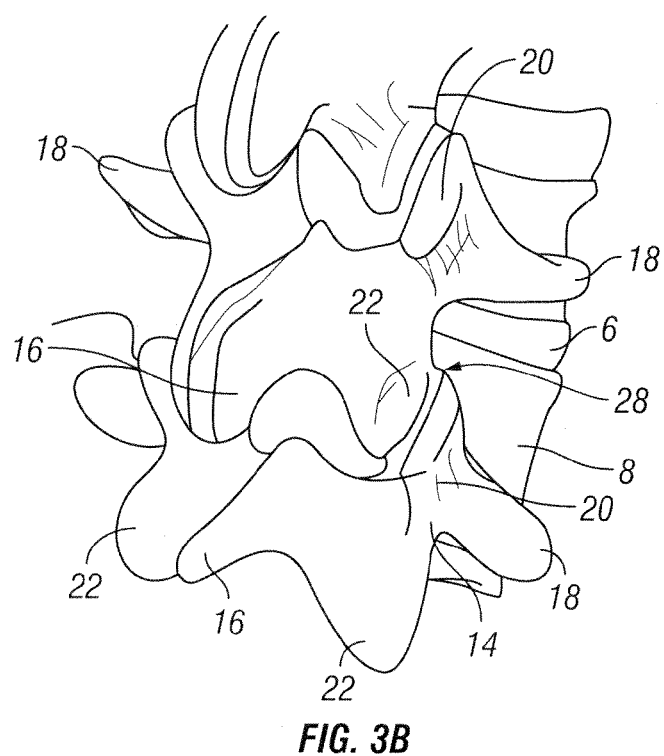

Throughout the drawings, the same reference numerals and characters, unless otherwise stated, are used to denote like features, elements, components, or portions of the illustrated embodiments. Moreover, while the present invention will now be described in detail with reference to the figures, it is done so in connection with the illustrative embodiments and is not limited by the particular embodiments illustrated in the figures.

DETAILED DESCRIPTION OF EMBODIMENTS OF THE INVENTION

In one aspect, embodiments of the present invention provide a method for accessing a facet joint, and which can further provide a path to the facet joint which is approximately perpendicular to the articular surfaces of the facet joint in a minimally invasive manner.

In one embodiment of the invention, general anesthesia is achieved and the patient is positioned prone on a turning frame or three-point head rest attached to the table. Skeletal traction is performed using tongs. The patient is prepped and draped using conventional sterile techniques. Pre-operative radiographic films may optionally be reviewed and any vertebral anomalies or variations are noted. In one embodiment, the spinous processes are palpated to identify the location of the cervical vertebrae.

Figure 7A:
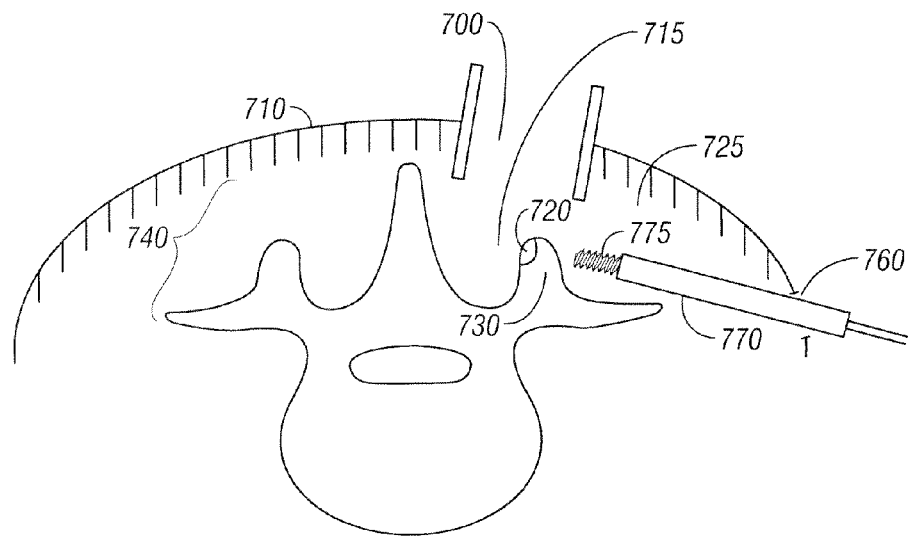
FIG. 7A is a cross-sectional view in the transverse plane of two minimally invasive incisions which can be used to provide access to a facet joint using a straight path.

In one embodiment, shown in FIG. 7A, an incision 700 is made through the skin 710 over the facet joint 715 of interest. The exposed skin edges and subcutaneous tissue are optionally injected with epinephrine 1:500,000 solution to facilitate hemostasis. Preferably, dissection is performed through the muscle tissue 725 overlying the facet joint 715. The incision 700 allows direct visualization of the facet joint 715, which includes a facet 720 on a superior and/or inferior articular process 730 of the posterior portion 740 of the vertebra. A soft tissue retractor 750, or a similar device, is used to maintain the incision 700 in a spread position to provide a pathway to maintain direct visual and physical access to the facet joint 715. The tissue retractor 750 can be a blade retractor, a tubular retractor, or another type of retractor.

The incision 700 is preferably less than about 3 cm. long, and more preferably less than about 2 cm. long. A larger incision can be formed to provide sufficient access to a particular facet joint 715. A separate incision 700 can be created in the skin 710 over each facet joint 715 to be treated.

Figure 11:
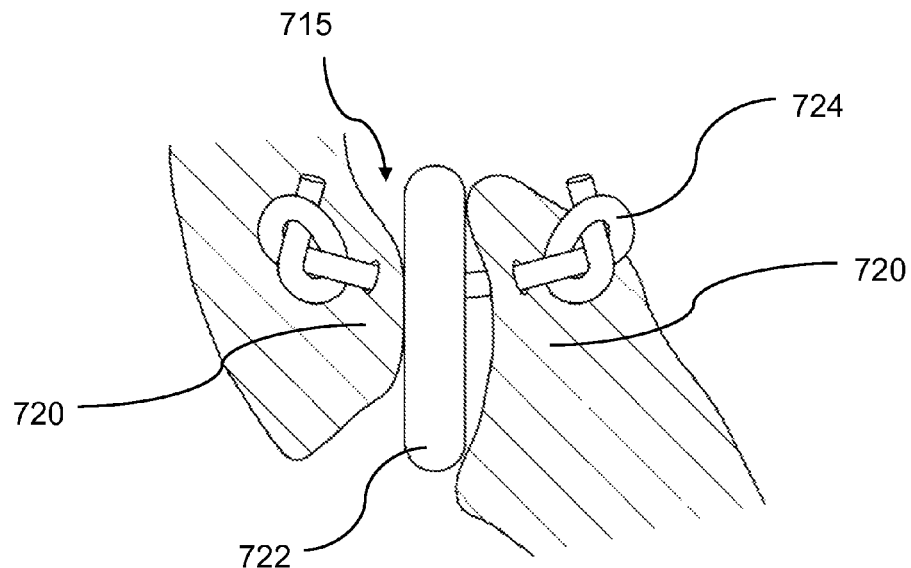
FIG. 11 is a side view of an embodiment of an implant in a facet joint with an embodiment of a fastening member through the facet joint.
Figure 12:
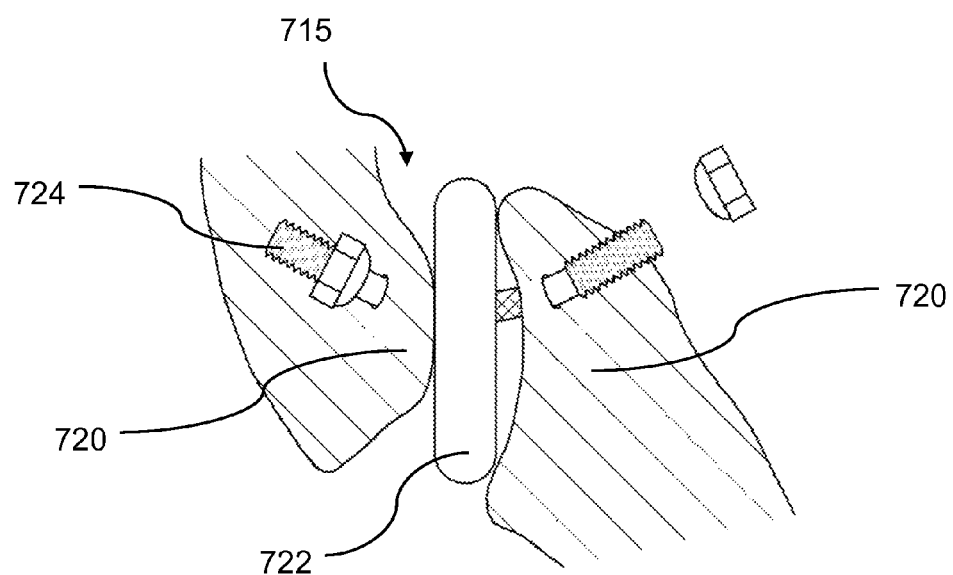
FIG. 12 is a side view of an embodiment of an implant in a facet joint with another embodiment of a fastening member through the facet joint.

The joint capsule of the facet joint may optionally be opened by incision or piercing. In certain embodiments, the facets 720 of the facet joint 715 are distracted to provide access to the joint space. In one embodiment, the facet joint 715 is prepared for insertion of an implant 722 within the joint, such as illustrated in FIGS. 11-12. For example, a joint capsule surrounding the facet joint can be opened, and at least a portion of the cartilage present within the joint 715 may be removed. Optionally, the facet surfaces 720 can be prepared for receiving an implant 722 by roughening them. A joint implant is then selected and inserted into the facet joint space through the incision 700.

A second incision 760 is then made at a particular distance from the first incision 700. The second incision 760 is preferably small, for example less than about 5 mm wide, or preferably less than about 3 mm wide. The second incision 760 may also be formed as a puncture wound in the skin 710. The second incision 760 is located such that an instrument 770 can be provided through the incision, and directed along a substantially straight path toward the facet joint 715. The distance between the first incision 700 and the second incision 760 is preferably between about 2 cm and about 20 cm, or more preferably between about 2 cm and about 10 cm, although distances outside of these ranges may also be used for particular applications.

In one embodiment, the path defines a trajectory such that the path is substantially perpendicular to the facet surfaces 720 of the facet joint 715 where they intersect (i.e., the angle between the path and the facet surfaces 720 is approximately 90 degrees), as shown in FIG. 7A. Non-orthogonal angles between the path and the facet surfaces 720 may also be used. Preferably, these angles are close to 90 degrees, such that the path intersects a portion of the surfaces 720 of both facets. For example, the angle between the path and the facet surfaces 720 may be greater than about 60 degrees, or preferably greater than about 80 degrees. Other angles between the path and the facet surfaces 720 may also be used for certain procedures in which access to the facets at a particular angle is desirable.

The instrument 770 can be provided with a blunt tip or alternatively with a sharpened tip, and is preferably pushed through the tissue 725 towards the facet joint 715 to create a direction of the path. Preferably, the second incision is provided at a distance from the first incision 700 that is not so large that the path from the second incision 760 to the facet joint 715 intersects or penetrates the peritoneum.

Figure 7B:
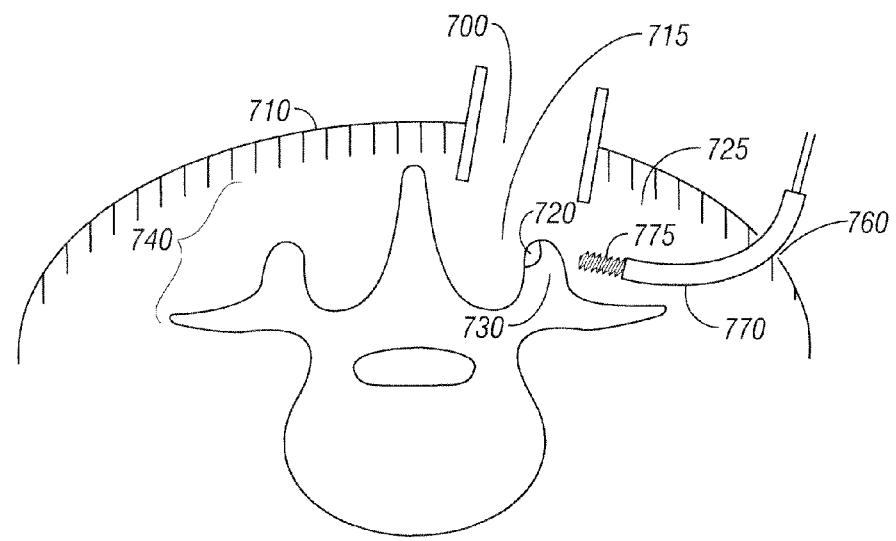
FIG. 7B is a cross-sectional view in the transverse plane of two minimally invasive incisions which can be used to provide access to a facet joint using a curved path.

In a further embodiment, the path between the second incision 760 and the facet joint 715 is curved, as shown in FIG. 7B. Such a curved path can allow more flexibility in selecting a location for the second incision with respect to the first incision. A portion of the curved path can be formed, for example, by inserting the instrument 770, which may be curved along the major axis, through the second incision and through the tissue 725 until it reaches the facet joint 715. Preferably, the path and instrument 770 are substantially perpendicular to the facet surfaces 720 where the path intersects the facet joint 715, as shown in FIG. 7B. Non-orthogonal angles between the path and the facet surfaces 720 may also be used, as described herein above.

The instrument 770 preferably includes a catheter, cannula, or other cylindrical or tubular housing. Optionally, the instrument 770 is provided in such a housing. In one embodiment, the instrument 770 includes a drill 775 configured to create a hole through the superior or inferior articular process 730, and preferably through the facet surfaces 720. The instrument 770 can also be used to form a hole through an implant inserted in the facet joint 715, if such implant is provided therein. The incision 700 allows direct visualization of the superior and/or inferior articular process 730 and the facet joint 715 associated with it during formation of holes by the instrument 770. This visualization enables the holes to be created in a desired location and for the position of the instrument 770 to be adjusted to achieve this.

After one or more holes are formed by the instrument 770 (or another manipulation of the facet joint 715 is performed), any resultant debris can be removed using suction or other techniques through the incision 700, which is maintained in an open position by the soft tissue retractors 750. After the holes are formed, a retaining member can be inserted therethrough to anchor the implant within the facet joint 715. Examples of such retaining members and anchoring procedures are provided in U.S. Patent Publication No. 2005/0177240. Alternatively, a screw or other fastening member 724 can be provided through the path formed using the instrument 770 to attach the facets 720 of the facet joint 715 together, thereby immobilizing the facet joint 715, as illustrated in FIGS. 11-12. Accessing the facet joint 715 via a path that is substantially perpendicular to the facet surfaces 720 allows a retaining member or a fastening member 724 to be positioned directly across the facet joint 715. Such positioning may result in better performance, stability, or the like than configurations in which such members provided at an oblique angle to the facet surfaces 720.

After one or more of the various procedures described herein are performed on the facet joint 715, the incisions 700 and 760 are then closed and allowed to heal. The method described herein may be repeated for each of a plurality of facet joints to be treated.

Figure 4A:
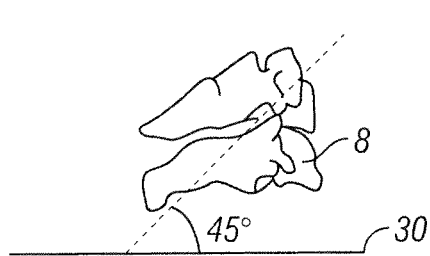
FIGS. 4A and 4B are schematic side and superior views, respectively, of a facet joint in the cervical vertebrae.
Figure 4B:
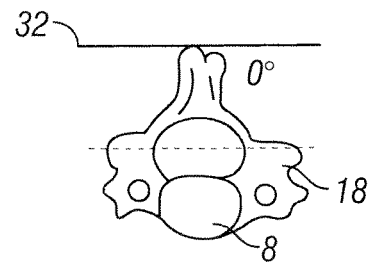
Figure 8:
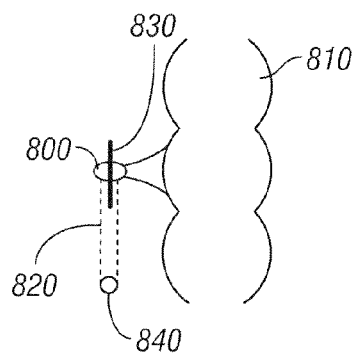
FIG. 8 is a schematic illustration of the approximate positions of two incisions which can be created to provide access to a facet joint associated with the C3-C7 vertebrae.

An exemplary configuration for the first incision 700 and second incision 760 which can be created to access a facet 800 associated with a facet joint of the C3-C7 vertebrae 810 is shown in FIG. 8. The approximate spatial orientation of the facet 800 is shown in FIGS. 4A and 4B. The surface of the facet 800 in the C3-C7 vertebrae 810 is approximately parallel to the frontal plane and is oriented at an angle of approximately 45 degrees to the transverse plane. The first incision 830 is created directly over the facet 800 of interest to provide access thereto, as described herein above. Although the first incision 830 is shown as being parallel to the vertebral column 810 in FIG. 8, any other orientation of the first incision 830 with respect to the vertebral column 810 can be used to provide access to the facet 800.

The second incision 840 is created substantially directly below the facet 800 (along the direction of the vertebral column) because of the substantially parallel orientation of the facet 800 with respect to the frontal plane as shown in FIG. 4B. The second incision 840 is located at a longitudinal distance that is several centimeters away from the first incision 830. This position allows a path 820 to be created between the second incision 840 and the facet 800 that is substantially orthogonal to the surface of the facet 800. The precise distance and orientation between the first incision 830 and the second incision 840 is preferably selected based on the particular orientation of the facet 800 of interest (which may vary slightly among the vertebrae 810), and the curvature of the instrument used to form the path between the second incision 840 and the facet 800. Although the techniques described herein may be more suitable for lumbar and thoracic vertebrae, such techniques may be used with the C3-C7 vertebrae if the path between the second incision 840 and the facet 800 is carefully selected using a particular curvature.

Figure 5A:
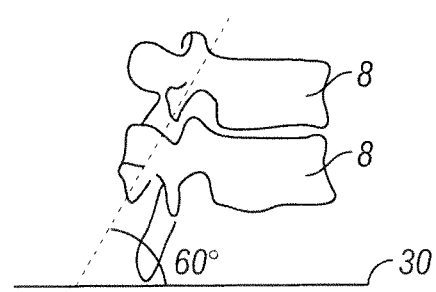
FIGS. 5A and 5B are schematic side and superior views, respectively, of a facet joint in the thoracic vertebrae.
Figure 5B:
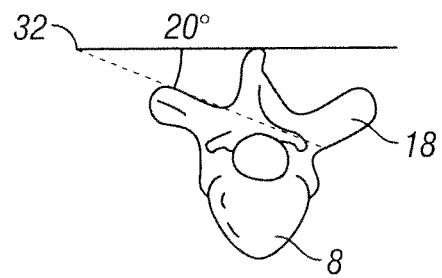
Figure 9:
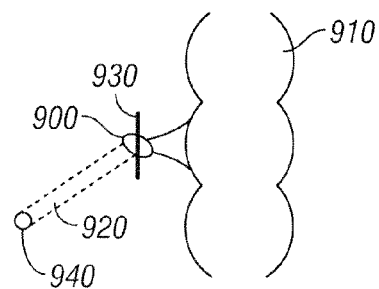
FIG. 9 is a schematic illustration of the approximate positions of two incisions which can be created to provide access to a facet joint associated with the thoracic vertebrae.

In a further embodiment, an exemplary configuration for the first incision 930 and second incision 940 which can be created to access a facet 900 associated with a facet joint of the thoracic vertebrae 910 is shown in FIG. 9. The approximate spatial orientation of the facet 900 is shown in FIGS. 5A and 5B. The surface of the facet 900 in the thoracic vertebrae 910 is approximately parallel to the frontal plane and is oriented at an angle of approximately 45 degrees to the transverse plane. The first incision 930 is created directly over the facet 900 of interest to provide access thereto, as described herein above. Although the first incision 930 is shown as being parallel to the vertebral column 910 in FIG. 9, any other orientation of the first incision 930 with respect to the vertebral column 910 can be used to provide access to the facet 900.

The second incision 940 is preferably created a few centimeters below the facet 900 (along the direction of the vertebral column) and several centimeters to the side thereof (in a lateral direction) based on the orientation of the facet 900 with respect to the transverse and frontal planes as shown in FIGS. 5A-5B. This position allows a path 920 to be created between the second incision 940 and the facet 900 that is substantially orthogonal to the surface of the facet 900 in the vicinity of the facet joint. The precise distance and orientation between the first incision 930 and the second incision 940 is preferably selected based on the particular orientation of the facet 900 of interest (which may vary slightly among the vertebrae 910) and the curvature of the instrument used to form the path between the second incision 940 and the facet 900. Also, the location of the second incision 940 is preferably selected to avoid any penetration of the peritoneum by the path 920.

Figure 6A:
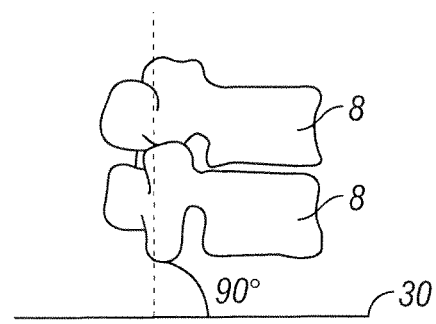
FIGS. 6A and 6B are schematic side and superior views, respectively, of a facet joint in the lumbar vertebrae.
Figure 6B:
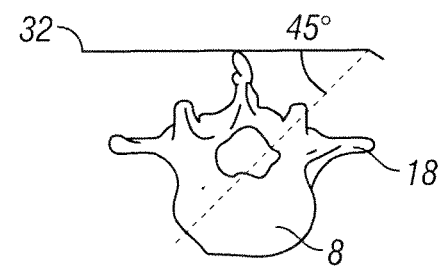
Figure 10:
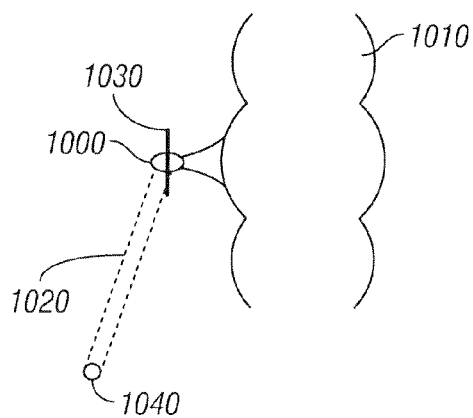
FIG. 10 is a schematic illustration of the approximate positions of two incisions which can be created to provide access to a facet joint associated with the lumbar vertebrae.

In a still further embodiment, an exemplary configuration for the first incision 1030 and second incision 1040 which can be created to access a facet 1000 associated with a facet joint of the lumbar vertebrae 1010 is shown in FIG. 10. The approximate spatial orientation of the facet 1000 is shown in FIGS. 6A and 6B. The surface of the facet 1000 in the thoracic vertebrae 1010 is oriented at an angle of approximately 45 degrees to the frontal plane and is approximately perpendicular to the transverse plane. The first incision 1030 is created directly over the facet 1000 of interest to provide access thereto, as described herein above. Although the first incision 1030 is shown as being parallel to the vertebral column 1010 in FIG. 10, any other orientation of the first incision 1030 with respect to the vertebral column 1010 can be used to provide access to the facet 1000.

The second incision 1040 is preferably created several centimeters below the facet 1000 (along the direction of the vertebral column) and a few centimeters to the side thereof (in a lateral direction) based on the orientation of the facet 1000 with respect to the transverse and frontal planes as shown in FIGS. 6A-6B. The larger distance between the facet 1000 and the second incision 1030 allows the path 1020 to be substantially orthogonal to the transverse plane and therefore substantially orthogonal to the surface of the facet 1000. The precise distance and orientation between the first incision 1030 and the second incision 1040 is preferably selected based on the particular orientation of the facet 1000 of interest (which may vary slightly among the vertebrae 1010) and the curvature of the instrument used to form the path between the second incision 1040 and the facet 1000. Also, the location of the second incision 1040 is preferably selected to avoid any penetration of the peritoneum by the path 1020.

The foregoing merely illustrates the principles of the invention. Various modifications and alterations to the described embodiments will be apparent to those skilled in the art in view of the teachings herein. It will thus be appreciated that those skilled in the art will be able to devise numerous techniques which, although not explicitly described herein, embody the principles of the invention and are thus within the spirit and scope of the invention. All patents, patent applications, and other publications cited herein are incorporated herein by reference in their entireties.

The invention claimed is:

1. A method for providing access to a spinal facet joint, the method comprising:
    providing a first incision directly over the facet joint, the first incision allowing direct visualization of a superior or an inferior articular process and the facet joint which includes a facet on the superior or the inferior articular process;
    retracting sides of the first incision to reveal the facet joint;
    creating a second incision at a particular distance from the first incision, wherein the second incision is ipsilateral to the facet joint;
    creating a path between the second incision and the facet joint, such that the path intersects an articular surface of each facet of the facet joint, the second incision provided at a distance from the first incision that is not so large that the path from the second incision to the facet joint intersects or penetrates the peritoneum; and
    positioning a fastening member across the facet joint.

2. The method of claim 1, wherein a length of the first incision is less than about 3 cm.

3. The method of claim 2, wherein a length of the second incision is less than about 5 mm.

4. The method of claim 2, wherein a length of the second incision is less than about 3 mm.

5. The method of claim 2, wherein the second incision is a puncture wound.

6. The method of claim 1, wherein a length of the first incision is less than about 2 cm.

7. The method of claim 1, wherein the sides are retracted using a tissue retractor.

8. The method of claim 7, wherein the tissue retractor is at least one of a blade refractor or a tubular retractor.

9. The method of claim 1, wherein an angle between the path and the articular surface is approximately 90 degrees.

10. The method of claim 1, wherein an angle between the path and the articular surfaces is greater than about 80 degrees.

11. The method of claim 1, wherein an angle between the path and the articular surfaces is greater than about 60 degrees.

12. The method of claim 1, wherein the path is created by inserting an instrument through the second incision until a distal end thereof reaches the facet joint.

13. The method of claim 12, wherein the instrument is substantially straight along a primary axis thereof.

14. The method of claim 12, wherein the instrument is curved along a primary axis thereof.

15. The method of claim 12, wherein the instrument includes a tubular housing.

16. The method of claim 12, wherein the instrument includes a drill.

17. The method of claim 12, further comprising the step of generating a hole in at least one facet of the facet joint using the instrument.

18. The method of claim 17, further comprising the step of inserting an implant within the facet joint.

19. The method of claim 18, further comprising the step of generating a hole in the implant using the instrument after the implant is inserted in the facet joint.

20. The method of claim 12, further comprising the step of inserting the fastening member across both facets of the facet joint using the instrument.

21. The method of claim 20, wherein the fastening member is a screw.

22. The method of claim 1, wherein the particular distance is between about 2 cm and about 20 cm.

23. The method of claim 1, wherein the particular distance is between about 2 cm and about 10 cm.

24. A method for treating a spinal facet joint, the method comprising:
  providing a first incision directly over the facet joint, the first incision allowing direct visualization of a first articular process and a second articular process of the facet joint;
  retracting sides of the first incision to reveal the facet joint;
  creating a second incision at a distance from the first incision, wherein the second incision is ipsilateral to the facet joint;
  creating a path between the second incision and the facet joint;
  creating a hole through the first articular process, through a facet surface of the facet joint, and through the second articular process; and
  positioning a fastening member across the facet joint.

25. The method of claim 24, wherein the second incision is a puncture wound.

26. The method of claim 24, wherein an angle between the path and the facet surface is approximately 90 degrees.

27. The method of claim 24, wherein an angle between the path and the facet surfaces is greater than about 60 degrees.

28. The method of claim 24, wherein the path is created by inserting an instrument through the second incision until a distal end thereof reaches the facet joint.

29. The method of claim 28, wherein the instrument is substantially straight along a primary axis thereof.

30. The method of claim 28, wherein the instrument is curved along a primary axis thereof.

31. The method of claim 28, further comprising the step of inserting an implant within the facet joint.

32. The method of claim 31, further comprising the step of generating a hole in the implant using the instrument after the implant is inserted in the facet joint.

33. The method of claim 24, wherein the distance is between about 2 cm and about 20 cm.

* * * * *